(12) United States Patent
Borden et al.

(10) Patent No.: US 11,141,546 B2
(45) Date of Patent: Oct. 12, 2021

(54) SYSTEMS AND METHODS FOR VENTILATION THROUGH A BODY CAVITY

(71) Applicants: The Regents of the University of Colorado, a Body Corporate, Denver, CO (US); Board of Regents for the University of Nebraska, Lincoln, NE (US)

(72) Inventors: Mark A. Borden, Boulder, CO (US); Benjamin S. Terry, Lincoln, NE (US)

(73) Assignees: The Regents of the University of Colorado, a Body Corporate, Denver, CO (US); Board of Regents of the University of Nebraska, Lincoln, NE (US)

( * ) Notice: Subject to any disclaimer, the term of this patent is extended or adjusted under 35 U.S.C. 154(b) by 31 days.

(21) Appl. No.: 16/179,024

(22) Filed: Nov. 2, 2018

(65) Prior Publication Data
US 2019/0070370 A1 Mar. 7, 2019

Related U.S. Application Data

(63) Continuation of application No. 14/256,488, filed on Apr. 18, 2014, now Pat. No. 10,124,126.

(60) Provisional application No. 61/813,626, filed on Apr. 18, 2013.

(51) Int. Cl.
| | |
|---|---|
| A61M 13/00 | (2006.01) |
| A61M 1/28 | (2006.01) |
| A61M 1/32 | (2006.01) |
| A61M 16/04 | (2006.01) |

(52) U.S. Cl.
CPC ............ *A61M 13/003* (2013.01); *A61M 1/28* (2013.01); *A61M 1/32* (2013.01); *A61M 16/04* (2013.01); *A61M 2202/0208* (2013.01); *A61M 2205/3344* (2013.01); *A61M 2205/3653* (2013.01); *A61M 2205/502* (2013.01); *A61M 2230/202* (2013.01); *A61M 2230/205* (2013.01); *A61M 2230/50* (2013.01)

(58) Field of Classification Search
CPC ........ A61M 1/28; A61M 1/32; A61M 13/003; A61M 13/006; A61M 16/04; A61M 2202/028; A61M 2205/3344; A61M 2205/3653; A61M 2205/502; A61M 2230/202; A61M 2230/205; A61M 2230/50; A61M 13/00; A61M 2202/0208
See application file for complete search history.

(56) References Cited

U.S. PATENT DOCUMENTS

| | | | | |
|---|---|---|---|---|
| 2004/0013662 | A1* | 1/2004 | Porter | A61P 29/00 424/94.61 |
| 2010/0204765 | A1* | 8/2010 | Hall | A61M 1/28 607/105 |
| 2012/0175305 | A1* | 7/2012 | Borden | B01J 13/04 210/644 |

\* cited by examiner

*Primary Examiner* — Tiffany Legette
(74) *Attorney, Agent, or Firm* — Brainspark Associates, LLC

(57) ABSTRACT

A system and methods for the delivery of oxygen through a body cavity of a subject using oxygen microbubbles. Through circulation of oxygen microbubbles through the body cavity, oxygen and carbon dioxide exchange may occur. Overall improvement in extending survival rate time during emergency situations caused by pulmonary or similar oxygen-intake restricting injury and/or failure may be achieved through use of the invented system and methods.

20 Claims, 8 Drawing Sheets

SYSTEMS AND METHODS FOR VENTILATION THROUGH A BODY CAVITY

CROSS REFERENCE TO RELATED APPLICATIONS

This application is a continuation of U.S. patent application Ser. No. 14/256,488, entitled "System and Methods for Ventilation Through a Body Cavity," filed Apr. 18, 2014, which in turn claims the benefit of U.S. provisional application 61/813,626 filed Apr. 18, 2013, each of which are incorporated by reference herein in their entireties.

FEDERAL FUNDING

This invention was made with government support under grant number CBET1059726 awarded by the National Science Foundation. The government has certain rights in the invention.

FIELD OF THE INVENTION

The invention relates generally to the delivery of oxygen to a subject. More particularly, the invention relates to the delivery of oxygen through a body cavity of a subject using oxygen microbubbles.

BACKGROUND OF THE INVENTION

Oxygen is one of the basic essentials for sustaining life. Today's medical technology can supply oxygen to patients experiencing pulmonary failure, otherwise known as respiratory failure. Pulmonary failure occurs when the lungs experience significant damage and are unable to supply the body and brain with oxygen. Pulmonary failure may be caused by a variety of conditions including, for example, lung cancer, physical trauma, acute respiratory distress syndrome (ARDS), aerosolized bioterrorism agents, and diseases such as severe acute respiratory syndrome (SARS), pneumonia, tuberculosis, sepsis, and other bacterial or viral infections, physical trauma, and chemical or smoke inhalation. Currently, oxygen can be supplied to patients experiencing pulmonary failure through mechanical ventilation (MV) or extracorporeal membrane oxygenation (ECMO). However, the mortality rate of patients receiving oxygen through MV or ECMO remains high.

MV has been an ineffective method for delivering oxygen to the body in certain cases because oxygen exchange is decreased by damage to the lung and because of increased stress caused to the injured lung by the treatment. As an example, for patients experiencing severe hypoxemia arising from lung injury MV may be inadequate owing to limited mass transfer in the injured lung; over-inflation, barotrauma and cyclic closing and reopening of the alveoli may further damage the lung and trigger a pulmonary and systemic inflammatory reaction that may lead to multiple system organ failure.

ECMO is a temporary artificial extracorporeal support of the respiratory system and/or cardiac system. ECMO was first used in an adult in 1972 to treat severe respiratory failure and in 1974 on the first newborn. Innovations in ECMO include the introduction of polymethylpentene hollow fibers with non-thrombogenic coatings and thin wire-reinforced cannula walls. ECMO use has historically centered on neonatal care. However, ECMO is an expensive alternative therapy with limited availability in hospitals and length of treatment. ECMO is able to bypass the injured lungs to deliver oxygen and allow the lungs to heal, however there is a high risk of thrombosis and contamination of the blood because it is removed from the body. Since ECMO is associated with significant complications, sometimes additional therapies are required such as the use of anticoagulants (heparin is standard). However, anticoagulants are often administered to the patient leading to additional adverse side effects. Additionally, ECMO is expensive and complex to operate, limiting its accessibility for emergency care.

Because of the high mortality rate, methods of bypassing the lungs and delivering oxygen directly to the body have been explored for many years. Research has focused on peritoneal oxygenation as a method of extrapulmonary respiration. The exchange of oxygen and carbon dioxide occurs through the large surface area of the membrane that lines the abdominal cavity, the peritoneum.

Previous methods include in situ extrapulmonary ventilation (EV). Success in oxygenating blood in situ has been achieved by circulating fluorocarbons, blood, and liposome-encapsulated hemoglobin (a synthetic oxygen carrier) through the intraperitoneal (IP) space, or cavity. Additional previous methods include the study of carriers for the delivery of oxygen. Carriers have included blood, perfluorocarbon (PFC), and synthetic hemoglobin carriers, for example TRM-645, which are effective. In contrast, pure oxygen gas has been shown not to be an effective carrier. None of the effective carriers, however, are both safe and economical. For example, PFCs are expensive to generate and evaporate into potent greenhouse gases creating a significant environmental concern. They are also very stable, tending to accumulate in biological systems in which they are used. Blood and products derived from blood (like synthetic hemoglobin carriers) suffer from scarcity and are relatively expensive to fabricate and store. Furthermore, EV ventilation requires high volumes of perfusate; therefore, a fluid that is economical and biodegradable is important. In additional, none of the previously developed methods have achieved certain components for extrapulmonary respiration: (1) delivery of an adequate supply of oxygen, (2) long-term safety for the patient, and (3) cost-effectiveness.

Another form of therapy explored to deliver oxygen systematically by circulating it through the IP space is a method that uses an oxygen microbubble (OMB) carrier. OMBs are oxygen filled bubbles that have a shell composed of a phospholipid monolayer. The phospholipid monolayer shell of an OMB has similar composition to lung surfactant and requires comparable physical properties, such as rapid adsorption to and mechanical stabilization of the gas/liquid interface and high gas permeability. Thus OMBs are also designed to mimic the mechanical and gas transport properties of the alveolus to deliver the oxygen payload and uptake carbon dioxide.

Previous research has focused on the delivery of OMBs through intravenous (IV) oxygen delivery. However, IV injection of OMBs is a one-way administration and does not allow for the circulation of microbubbles into and out of the body to both deliver oxygen and remove carbon dioxide. Delivering oxygen using and IV appears to be a promising method for short-term rescue, but the prolonged continuous infusion of oxygen microbubbles into the bloodstream poses significant challenges for clinical translation, including the potential for embolism, thrombosis, immunogenicity and toxicities of lipid and saline load. For example, with IV injection of OMBs, any oxygen inspired through the lungs can be absorbed by the microbubbles and can cause long-circulating bubbles that may cause embolism or other problematic conditions, such as those observed in decompression sickness. Further, with the potential for embolism, IV injection of microbubbles requires a strict upper limit on the microbubble size (<10 micrometers) and on the microbubble volume fraction (<70%).

Still another problem with IV injection of OMBs is that any nitrogen inspired through the lungs, such as that found in air, will be absorbed by the microbubbles. Thus, the microbubbles will exchange oxygen for nitrogen. The nitrogen-containing microbubbles will be persistent, which can lead to serious problems, such as those observed during decompression sickness and embolism (thus leading to severe morbidity and death). In addition, intravenous oxygenation using OMBs cannot support long-term ventilation due to the lipid and saline load from continuous infusion.

A demand therefore exists for a system and method for delivery of oxygen to a subject that is more effective and efficient than the current systems and methods presently available. The invention satisfies this demand.

SUMMARY OF THE INVENTION

The invention is a system and methods that circulates oxygen microbubbles (OMBs) through a body cavity. Although the invention is discussed in reference to the intraperitoneal (IP) cavity, the invention is also applicable to other cavities of the subject such as the gastrointestinal (GI), pleural, cranial, vertebral, pericardial and other cavities as more fully described below. The invention delivers OMBs to the body via circulation through a body cavity using an oxygen carrier and perfusion apparatus to provide for safe and effective ventilation.

According to the invention, OMBs are designed for high oxygen carrying capacity, high oxygen delivery rate and sufficient stability for storage and transport. Direct systemic oxygenation by injecting OMBs into the peritoneal space is a radical change from existing oxygen delivery platforms. The procedure and apparatus for circulating OMBs through the peritoneal cavity is simple and straightforward, and the therapy precludes the need for an extracorporeal loop to circulate blood, thus potentially circumventing the complications from thrombosis and intracranial hemorrhage presented by ECMO.

Circulating OMBs through a body cavity requires less equipment and technical expertise than initiating and maintaining an ECMO circuit. Thus, body cavity ventilation using OMBs may provide extrapulmonary ventilation (EV) therapy to medical facilities that presently lack the funding or highly trained personnel required for operating an ECMO system.

By circulating OMBs in the body cavity, oxygen and carbon dioxide exchange occurs across the peritoneum, the membrane of the abdominal cavity. Additionally, unlike IV injection of microbubbles which cannot remove carbon dioxide, a body cavity injection and circulation of OMBs according to the invention can beneficially remove carbon dioxide. Additionally, the IP injection of OMBs, for example, is not subject to a strict upper limit of the microbubble size and volume fraction since the microbubbles are injected into the IP space (not the vasculature) and can thus easily be removed. This provides oxygen to a subject, for example after it experiences a right pneumothorax. This significantly extends life in a subject with an acute lung injury hypoxemia or similar situation in which the lung function is sub-optimal.

Direct systemic ventilation by circulating OMBs through the body cavity space is a radical change from existing oxygen delivery platforms. For example, the invention may be used to supplement ventilation in cases of airway failure, lung injury, respiratory distress, cardiac arrest, or other situations in which lung function is sub-optimal. The invention also precludes the need for an extracorporeal loop, thus potentially circumventing the complications of thrombosis and immune reaction presented by the artificial surfaces exposed by ECMO. The prospect of providing a bridge to, or even supplanting ECMO, may significantly reduce the cost and complexity of EV.

The ability to deliver oxygen via a body cavity may also have significant clinical implications. For example, acute severe hypoxia of any origin (due to airway obstruction or due to other causes) results in irreversible brain injury within minutes. Administration of readily accessible oxygen-bearing microbubbles may prevent the morbidity and mortality associated with acute hypoxia in many subjects such as human subjects. In addition, subjects suffering from lung injury, which represent a significant percentage of those requiring intensive care, may benefit from the delivery of oxygen that offers minimally invasive extrapulmonary oxygen supplementation. Thus, ventilator-induced lung injury may be minimized while avoiding critical hypoxia. Increasing systemic oxygen saturations may improve hypoxic pulmonary vasoconstriction and reduce pulmonary vascular resistance in subjects with acute exacerbations of pulmonary hypertension. Infants, for example, born with cyanotic congenital heart disease, could benefit from an effective delivery of oxygen that may lessen their hypoxemia preoperatively, as well as during the early postoperative recovery period. This therapy could also provide care for cases of irreversible pulmonary failure and, hence, act as a bridge to lung transplant. This work may be translated to a medical therapeutic device with the aim of replacing or augmenting ECMO with a less-invasive method of ventilation.

According to the invention, OMBs are injected into a body cavity and allowed some time to deliver oxygen and absorb carbon dioxide, followed by a saline flush to remove them from the cavity, followed by another injection of OMBs into the cavity. This process cycle is repeated as necessary. In the alternative, OMBs may be continuously circulated through the cavity to release oxygen and absorb carbon dioxide and other gases.

Since blood is oxygenated by OMBs administered through the body cavity, the infusion of OMBs directly into circulation is avoided. In addition, the upper size limit (about 10 μm diameter) is not required to avoid vascular occlusion. In certain embodiments, larger microbubbles (about 10-25 μm diameter) can be perfused through the body cavity without fear of occlusion because they are separated by gas-permeable membranous tissue from the intravascular space. Thus, the effects of larger microbubble size distributions on microbubble suspension viscosity and oxygen-release rate (at equivalent volume fraction) may be measured. According to the invention, microbubbles may be between 1-25 μm in diameter with larger microbubbles being about 9-21 μm in diameter and smaller microbubbles being about 1-8 μm in diameter. However, it is contemplated that microbubbles may be between 1-100 μm in diameter and even between 1-500 μm in diameter. In addition, mixtures of microbubbles may comprise microbubbles of different sizes. The sizes of the OMBs contained within any one mixture may be only smaller microbubbles, only larger microbubbles or a combination of both smaller and larger microbubbles.

In embodiments in which a perfusate is administered, the perfusate may be about 60%, 65%, 70%, 75%, 80%, 85%, 90%, or 95%. In certain other example embodiments, the OMB perfusate may be between 10%-90%.

One advantage of the invention over previously developed methods for extrapulmonary respiration is that the invention delivers an adequate supply of oxygen, provides long-term safety for the subject, and is cost-effective.

One advantage of the invention is that problems associated with ECMO are addressed and have the potential to significantly increase survivability of reversible pulmonary failure caused by pathologies and dysfunctions such as heart disease, chronic lower respiratory disease, accidents, influenza and pneumonia, airway failure, lung injury, respiratory distress syndrome, and other causes. In addition, the invention may help subjects survive avian flu and severe acute respiratory syndrome (SARS).

Other advantages of the invention include: reduced thrombogenic and immunogenic effects owing to lack of direct contact with blood, reduced risk of embolism by the OMBs or their lipid remnants because they are not in circulation, and the possibility of an input/output line to remove carbon dioxide in addition to providing oxygen.

An additional advantage of the invention is stability of the OMBs. OMBs are stable at high volume fractions (>90%) for several weeks in refrigerated storage.

Another advantage is that OMBs administered intravenously (<70 vol %) possess a rapid dissolving property and release of oxygen in the presence of oxygen-deficient media in vitro.

Additionally, OMBs according to the invention assist in further sustaining life during 15 minutes of complete tracheal occlusion in vivo. Thus, OMBs are a promising platform for non-extracorporeal oxygen delivery.

These and other features, aspects, and advantages of the invention will become better understood with regard to the following description, appended claims, and accompanying drawings.

DETAILED DESCRIPTION OF EXAMPLE EMBODIMENTS

Figure 1:
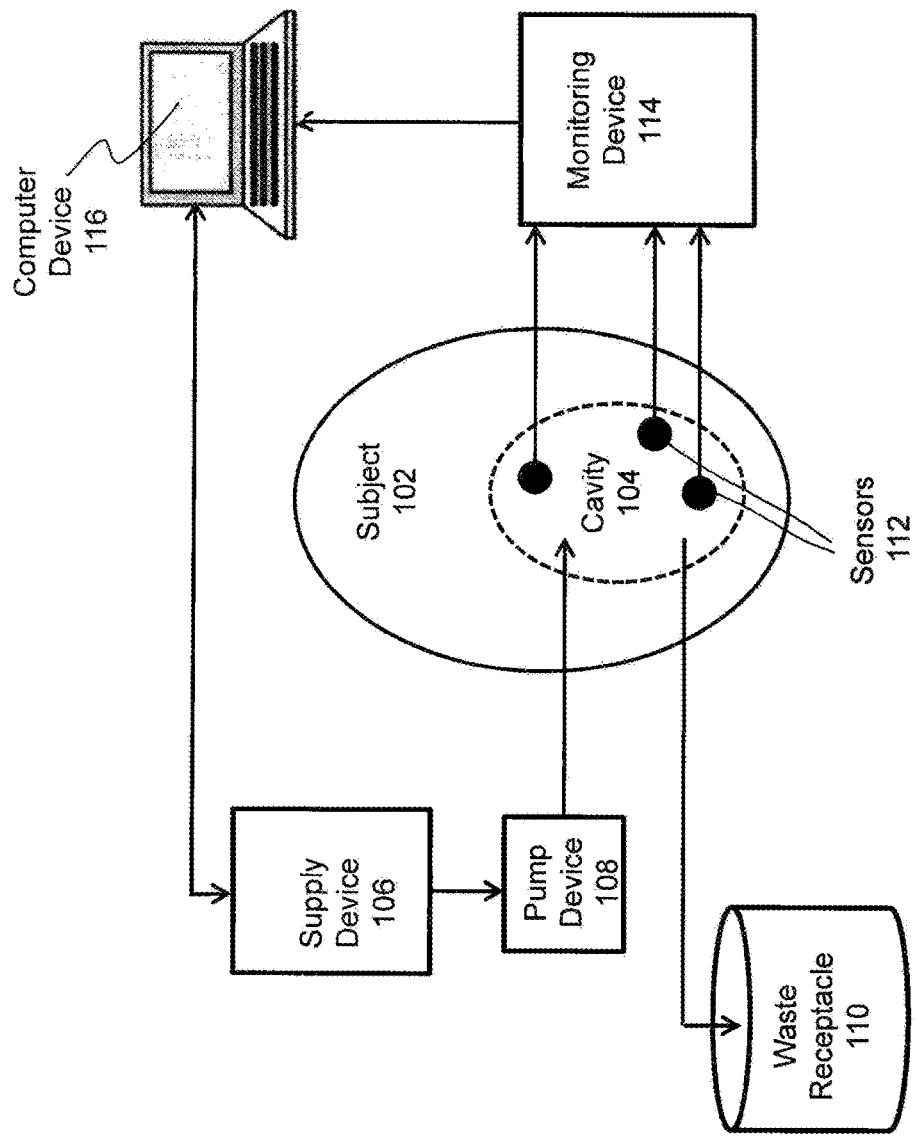
FIG. 1 illustrates an example embodiment of the ventilation system according to the invention.

FIG. 1 illustrates an example embodiment of the ventilation system 100. In this example embodiment, a subject 102 is treated with oxygen microbubbles (OMB) dispensed from a supply device 106 through the subject's body cavity 104 by a pump device 108. As OMBs from the supply device 106 are pumped into the body cavity 104 of the subject 102, waste is simultaneously removed from the subject and dispensed to the waste receptacle 110. The monitoring of several life sustaining data is performed with sensors 112 connected to the subject 102 and the monitoring device 114. Data include, for example, intra-abdominal pressure. The intra-abdominal pressure is measured to avoid high internal pressures that could damage the body's internal organs. Other data that may also be monitored include blood gas levels of oxygen and carbon dioxide, heart pulse, blood pressure, heart ejection faction and similar cardiac data. The monitoring device 114 transmits the data to a computer device 116 where the data is processed, for example, tabulated into a database, analyzed, and/or used to provide feedback to the supply device 106, for example to adjust the amount of OMB delivered to the subject 102. It is also contemplated that the supply device 106 transmits information to the computer device 116 for processing, for example, to adjust the data the sensors 112 monitor.

Figure 2:
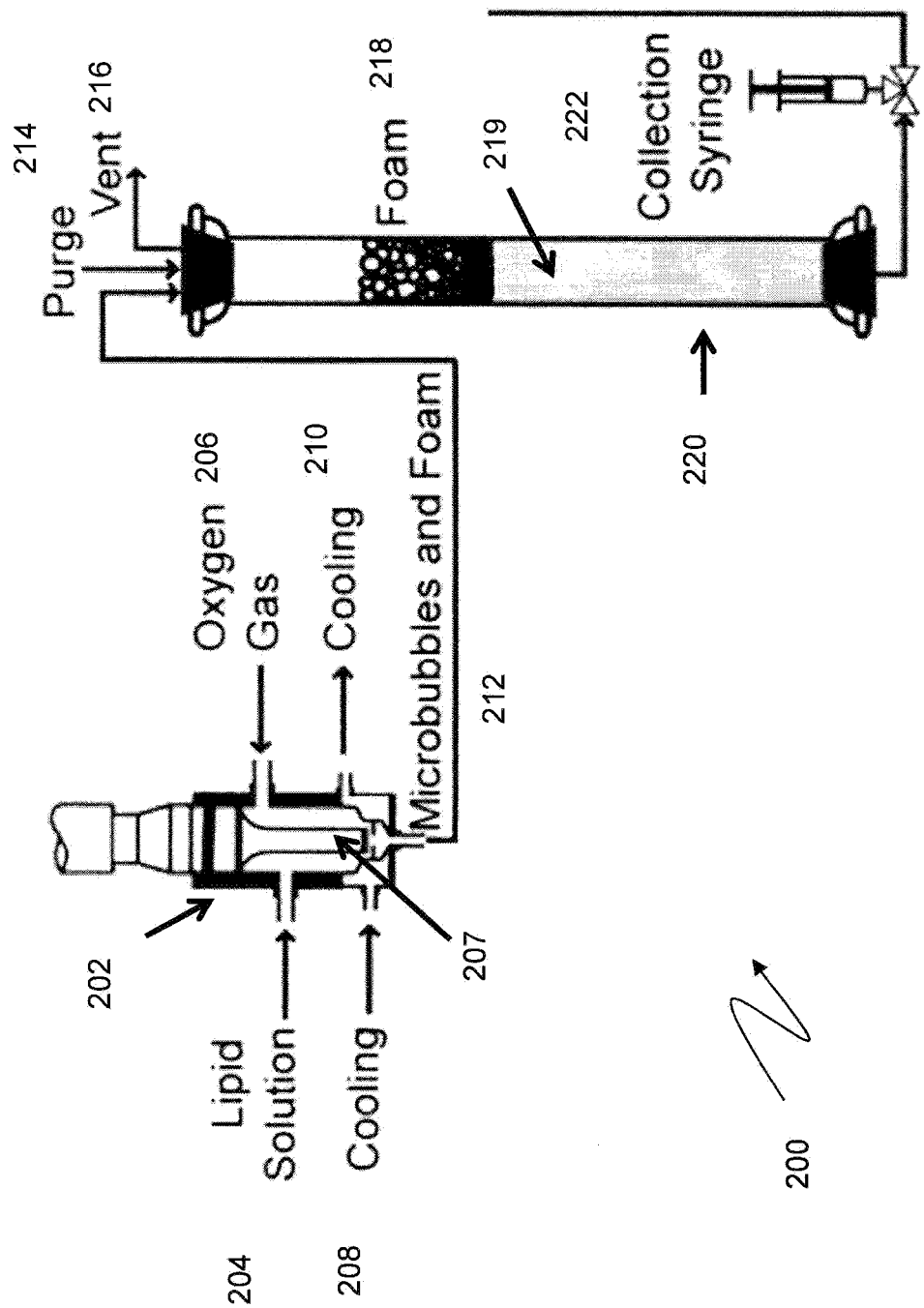
FIG. 2 illustrates an example embodiment of a supply device according to the invention.

FIG. 2 illustrates an example embodiment of a supply device 200 according to the invention. The supply device 200 includes a reaction chamber 202 with inlets for a lipid solution 204, and oxygen gas 206. The lipid solution 204 and oxygen gas 206 are mixed to create a mixture 207, which is then cooled. The mixture 207 is cooled using material such as air or liquid passing through an inlet 208 and outlet 210. In this process, a mix 212 of microbubbles and foam is created. The microbubbles and foam mix 212 is passed to a collection container 220. A solution 214, such as saline, is purged into the collection container 220 to combine with the microbubbles and foam mix 212. The collection container 220 includes a vent 216 for the discharge of gas. As the microbubbles and foam mix 212 combine with solution 214, ambient gas is vented 216 and the foam 218 separates from the microbubbles 219. The microbubbles 219 are then collected in a syringe 222, centrifuged and stored for future use.

Figure 3:
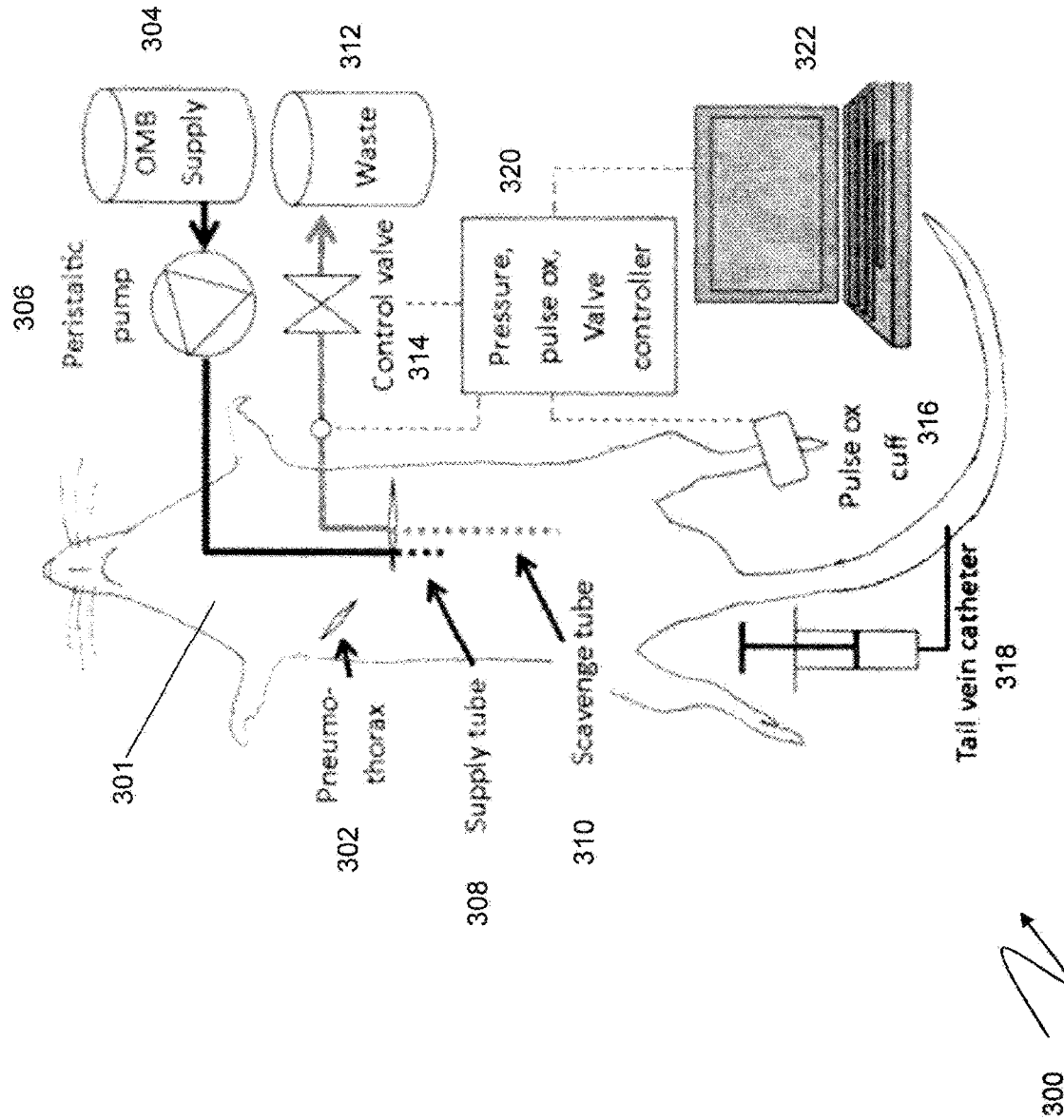
FIG. 3 illustrates one embodiment of a ventilation system used in the delivery of oxygen to a subject according to the invention.

FIG. 3 illustrates one embodiment of a ventilation system 300 used in the delivery of oxygen to a subject according to the invention. In this example embodiment, a subject 301 has a right pneumothorax 302. Cardiac arrest eventually follows a right pneumothorax and is caused by lack of blood oxygen (hypoxemia) and by elevated carbon dioxide levels and subsequent low blood pH (acidosis) that result from pulmonary failure. To keep the subject alive longer while life-saving treatment can be administered, the ventilation system 300 according to the invention is employed. A small incision is made into the abdomen of the subject 301 to give access to the IP cavity. Oxygen microbubbles from the supply device 304 are circulated into the IP cavity though a supply tube 308 with a peristaltic pump 306. Additionally a scavenge tube 310 is used to remove fluid waste 312, which may be controlled by a valve 314.

The effectiveness of IP extrapulmonary respiration is established by measuring and monitoring several life sustaining data. Intra-abdominal pressure may be measured at the supply tube 308 inlet. This is measured to avoid high internal pressures that could damage the body's internal organs. The blood gas levels of oxygen and carbon dioxide, heart pulse, blood pressure, heart ejection faction. Similar cardiac data may be measured with a paw cuff pulse 316 or similar medical device and perform periodic blood draws. Additionally drug dosage in the blood may be measured through a catheter 318. Measuring and monitoring these and other life sustaining data may be performed with a monitoring device 320 and viewed on a monitor of a computer device 322.

In an alternate embodiment, ventilation is performed through the gastrointestinal (GI) space. The system setup for perfusing the GI is identical to that shown in FIG. 3 with the exception that the small intestine is resected at the duodenum and distal ileum with the mesentery left intact. The supply tube is inserted into the resected duodenum, the scavenge tube is inserted into the resected distal ileum, and microbubbles from the supply device are pumped into and through the entire length of the small bowel.

Figure 4:
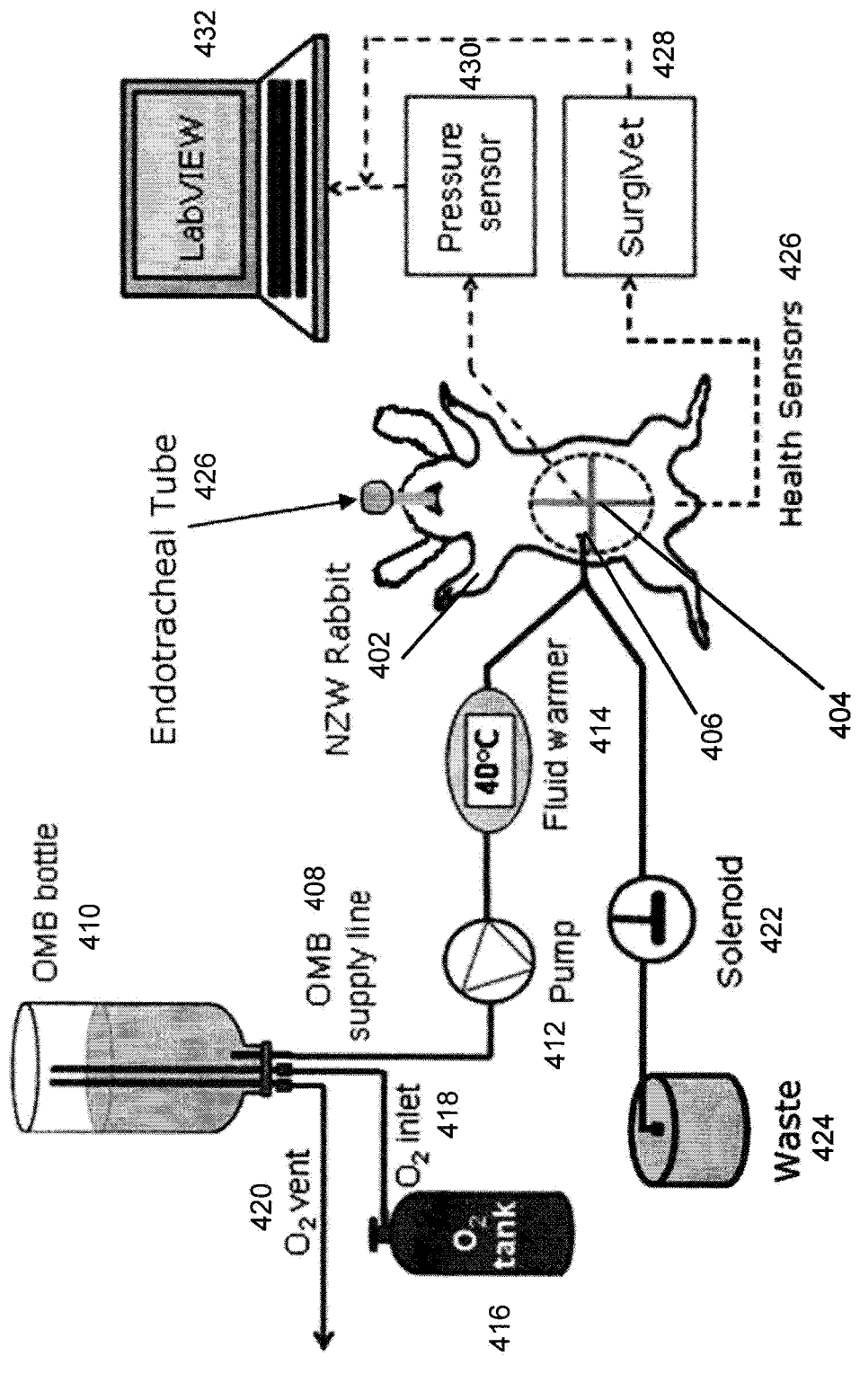
FIG. 4 illustrates another embodiment of a ventilation system used in the delivery of oxygen to a subject according to the invention.

FIG. 4 illustrates another embodiment of a ventilation system 400 used in the delivery of oxygen to a subject according to the invention. In this example embodiment, a subject 402 is connected to the system 400 through its pleural cavity 404 with an inlet/outlet tube 406. The inlet/outlet tube 406 allows the subject 402 to receive oxygen microbubbles from a supply device 410 through a pump 412. The microbubbles are warmed using fluid warmer device 414.

The supply device 410 includes an oxygen tank 416 connected to an oxygen inlet 418 that prevents the supply device 410 from pressurizing while OMBs are pumped into the subject 402. There is additionally an oxygen vent 420 to assist in maintain ambient pressure in the supply device 410. The inlet/outlet tube 406 additionally allows for an expulsion of waste from the subject 402 from the pleural cavity 404. The expulsion of waste may be controlled by a solenoid valve 422, which allows the waste to drain into a waste receptacle 424. As this procedure of OMB injection is occurring, the subject's vital data is monitored with a number of health sensors 426 that are connected to a monitoring device 428. Additionally, pressure may be monitored by a pressure sensor 430. Health sensors 426 and pressure sensor 430 may be connected to a computer device 432 that may tabulate the data into a database, analyze the data, and/or used the data to provide feedback to one or more parts of the system 400. As an example, the machine computer device 432 may be connected to the supply device 410 to monitor and/or automate the injection time or quantity of OMBs.

Figure 5:
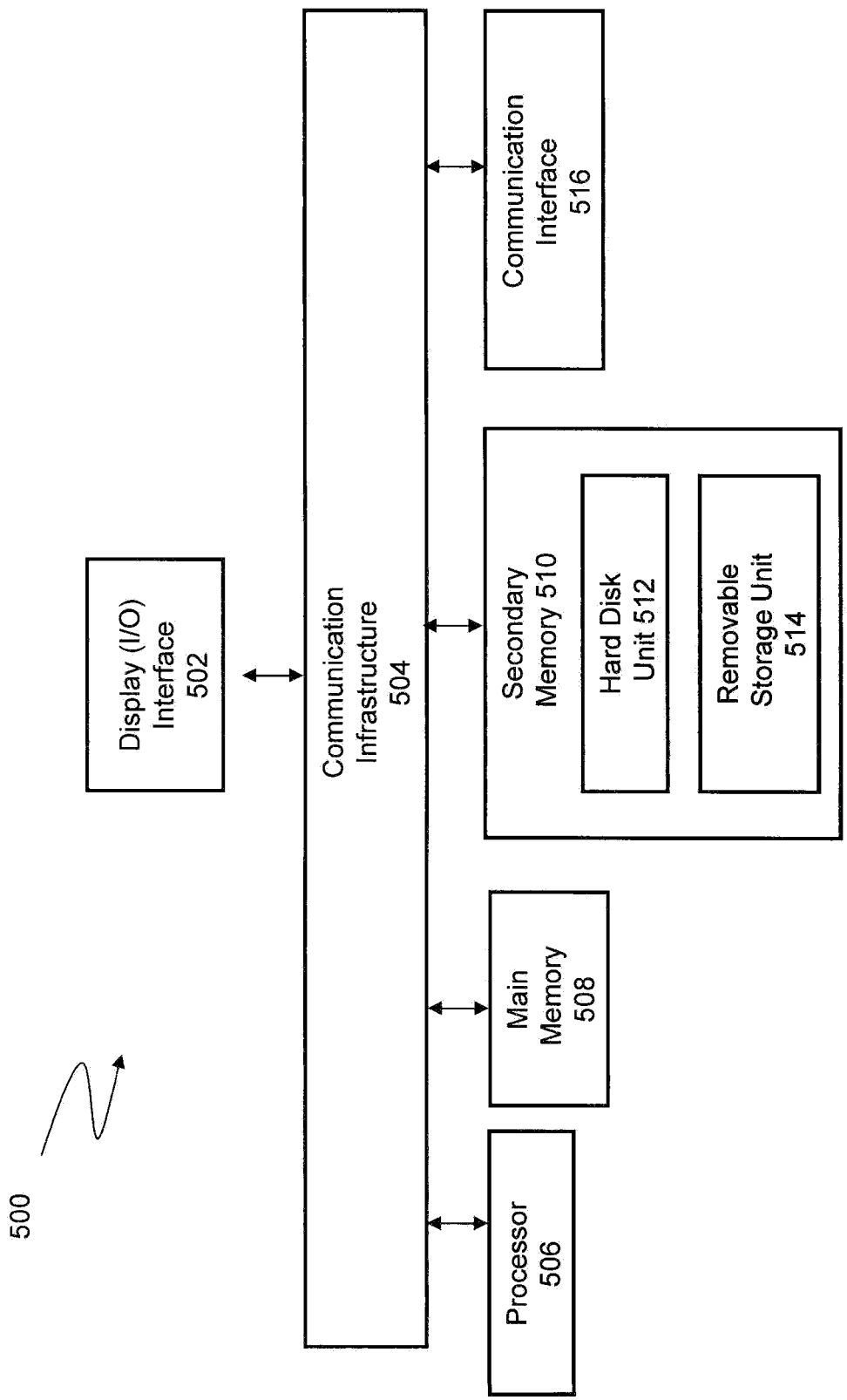
FIG. 5 illustrates an exemplary computer system according to the invention.

FIG. 5 illustrates an exemplary computer device 500 that may be used to implement the methods according to the invention. One or more computer systems 500 may carry out the methods presented herein as computer code.

Computer device 500 includes an input/output display interface 502 connected to communication infrastructure 504—such as a bus—that forwards data such as graphics, text, and information, from the communication infrastructure 504 or from a frame buffer (not shown) to other components of the computer device 500. The input/output display interface 502 may be, for example, a keyboard, touch screen, joystick, trackball, mouse, monitor, speaker, printer, Google Glass® unit, web camera, any other computer peripheral device, or any combination thereof, capable of entering and/or viewing data.

Computer device 500 includes one or more processors 506, which may be a special purpose or a general-purpose digital signal processor configured to process certain information. Computer device 500 also includes a main memory 508, for example random access memory (RAM), read-only memory (ROM), mass storage device, or any combination thereof. Computer device 500 may also include a secondary memory 510 such as a hard disk unit 512, a removable storage unit 514, or any combination thereof. Computer device 500 may also include a communication interface 516, for example, a modem, a network interface (such as an Ethernet card or Ethernet cable), a communication port, a PCMCIA slot and card, wired or wireless systems (such as Wi-Fi, Bluetooth, Infrared), local area networks, wide area networks, intranets, etc.

It is contemplated that the main memory 508, secondary memory 510, communication interface 516, or a combination thereof, function as a computer usable storage medium, otherwise referred to as a computer readable storage medium, to store and/or access computer software including computer instructions. Certain embodiments of a computer readable storage medium do not include any transitory signals or waves. For example, computer programs or other instructions may be loaded into the computer device 500 such as through a removable storage device, for example, a floppy disk, ZIP disks, magnetic tape, portable flash drive, optical disk such as a CD or DVD or Blu-ray, Micro-Electro-Mechanical Systems (MEMS), nanotechnological system. Specifically, computer software including computer instructions may be transferred from the removable storage unit 514 or hard disc unit 512 to the secondary memory 510 or through the communication infrastructure 504 to the main memory 508 of the computer device 500.

Communication interface 516 allows software, instructions and data to be transferred between the computer device 500 and external devices or external networks. Software, instructions, and/or data transferred by the communication interface 516 are typically in the form of signals that may be electronic, electromagnetic, optical or other signals capable of being sent and received by the communication interface 516. Signals may be sent and received using wire or cable, fiber optics, a phone line, a cellular phone link, a Radio Frequency (RF) link, wireless link, or other communication channels.

Computer programs, when executed, enable the computer device 500, particularly the processor 506, to implement the methods of the invention according to computer software including instructions.

The computer device 500 described herein may perform any one of, or any combination of, the steps of any of the methods presented herein. It is also contemplated that the methods according to the invention may be performed automatically, or may be invoked by some form of manual intervention.

The computer device 500 of FIG. 5 is provided only for purposes of illustration, such that the invention is not limited to this specific embodiment. It is appreciated that a person skilled in the relevant art knows how to program and implement the invention using any computer system.

The computer device 500 may be a handheld device and include any small-sized computer device including, for example, a personal digital assistant (PDA), smart hand-held computing device, cellular telephone, or a laptop or netbook computer, hand held console or MP3 player, tablet, or similar hand held computer device, such as an iPad®, iPad Touch® or iPhone®.

Figure 6:
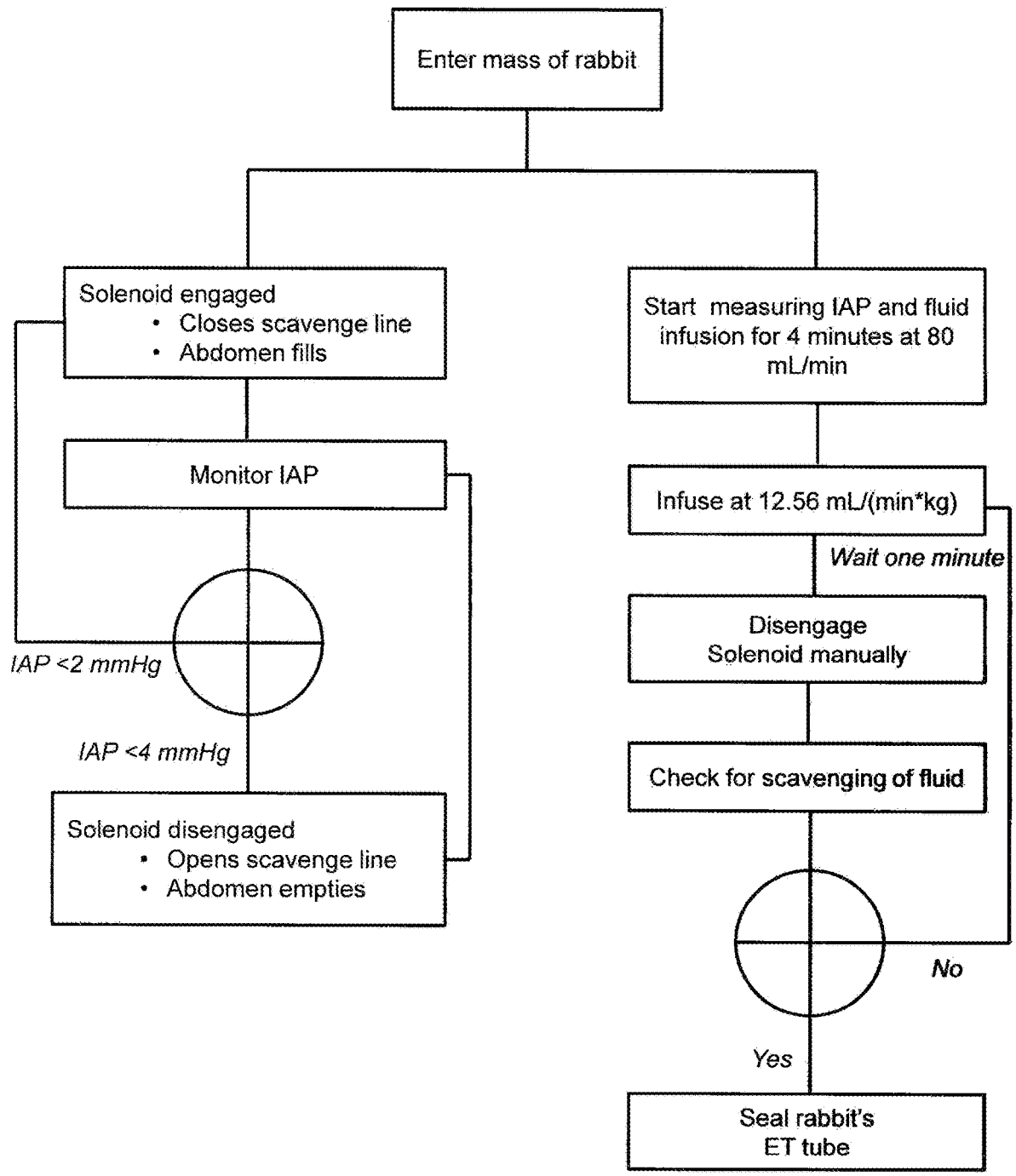
FIG. 6 illustrates an embodiment of the control scheme to monitor the perfusion of OMBs during delivery of oxygen to a subject according to the invention.

FIG. 6 is an example embodiment of the control system schematic that may be implemented at the solenoid valve to control the cavity pressure between the subject and the waste receptacle. Through monitoring the cavity pressure, the solenoid valve may be opened to relieve and lower pressure within the cavity or may be closed to increase pressure within the cavity. The opening and closing of the valve may be automated with use of the control system implemented to the computer device or may be manual with the control system providing an alarm.

Examples

OMB Production:

In an example embodiment, lipids are mixed at a 9:1 molar ratio of distearoyl phosphatidylcholine (DSPC) to poly(ethylene glycol)-40 stearate (PEG40S) in saline and sonicated at low power to create the small, unilamellar liposomes. $O_2$ and liposomes (5 mg/mL) are then combined in the reaction chamber, where a high-power, ½-inch diameter, 20-kHz sonicator tip emulsifies the oxygen gas into micrometer-scale spheres around which phospholipid adsorbs from vesicles and micelles and self-assembles into a highly condensed (solid) monolayer coating. OMBs are separated from macroscopic foam in a subsequent flotation container and collected in syringes and centrifuged (500 g for 3 min) to form concentrated OMBs. The sonication chamber and container are jacketed with circulating coolant to maintain a constant temperature of 20° C.

OMBs are fabricated for live animal testing, in which four factors are investigated: perfusate, perfusion rate, motility drug, and method (IP or GI). OMB perfusate at 70% and 90% indicate the volume fraction of oxygen in the OMB emulsion. At 70%, the OMB emulsion's rheological properties are similar to saline and the perfusate is expected to circulate well through the IP space.

OMB Size Distribution Measurements:

OMB size distribution is varied by choosing different residence times in the flotation container (e.g., 153 min for a 10-μm diameter cut-off; 38 min for a 20-μm diameter cut-off). Size distribution is measured, for example, by electrical capacitance, light extinction/scattering, flow cytometry scatter, and optical microscopy. Alternatively, size selection may be unnecessary and may be removed from the process. OMB volume fraction is measured, for example, by gravimetric analysis and varied from 50-90 vol % by dilution with saline. Microbubble size and concentration is measured over time to investigate coalescence, Ostwald ripening and stability in storage.

OMB Dissolution in Oxygen-Depleted Media:

Clinical translation of OMB technology to treat hypoxemia requires quantitative modeling of the pharmacokinetics of oxygen delivery, whether administered through the IV, IP or GI route. A model for single OMB dissolution in an oxygen-depleted medium with the presence of venous gases (30 mmHg $O_2$, 600 mmHg $N_2$ and 50 mmHg $CO_2$) has been developed. Results demonstrate the microbubble exhibits two dissolution regimes. First, rapid dissolution occurs as $O_2$ dissolves out, even as $N_2$ and $CO_2$ counter-diffuse into the bubble. Second, $O_2$ is depleted and slower dissolution occurs as $N_2$ and $CO_2$ dissolve out. For a 20-μm diameter microbubble, most of the oxygen is released within 10 s. The bubble then carries $N_2$ and $CO_2$ (therefore acting as a blood gas scrubber for non-oxygen species).

The simulation results indicate that the highest rate of oxygen transfer for the suspension occurs with the minimal OMB residence time in the IP space. Thus, rapid mixing should provide high mass transfer coefficients for both OMB oxygen release and oxygen transfer in the fluid medium to the parietal peritoneum and visceral peritoneum membranes. The results also indicate that oxygen-release rate increases substantially for larger microbubbles. It is expected that mixing conditions (i.e., viscosity) will dominate the rate of oxygen release.

Oxygen-Release Rate Measurements:

Three trials (three measurements per trial) are taken for each OMB flow rate and size distribution. Oxygen content is plotted versus time, and the linear regime is used to determine the oxygen-release rate (ng/s). The oxygen-release rate is compared for microbubbles of two different size distributions (1-10 μm diameter vs. 10-20 μm diameter), each at three different OMB flow rates (1, 10 and 20 mL/min) and three different volume fractions (50, 70 and 90%).

IP Ventilation of Rat Model In Vivo:

Using the system according to the invention, rats experienced a right pneumothorax after generally anesthetized by isoflurane (5% induction to effect) followed by sodium pentobarbital (50 mg/kg, intramuscular). Anesthesia depth is monitored and OMB perfusate is pumped into the IP space through a small incision in an upper quadrant of the abdomen. The IP incision is sutured/glued around the supply and scavenger tubing to form a seal. Intra-abdominal pressure is maintained at 8 mmHg through the use of a fluidic control solenoid valve and pressure catheter at the scavenger tube exit. Intra-abdominal pressure of 8 mmHg is used because it is typical of human insufflation pressures during laparoscopic surgery. Cardiac arrest will eventually follow pneumothorax and is caused by lack of blood oxygen (hypoxemia) and by elevated carbon dioxide levels and subsequent low blood pH (acidosis), which result from pulmonary failure. The effectiveness of IP EV is established from periodic tail-vein blood draws (5-minute intervals, total draws less than 1% body weight) and measurement of blood oxygen, carbon dioxide, pH, osmolality levels, and general blood chemistry.

Fluids used as a perfusate are saline as a control or a solution with an OMB concentration of 70% or 90% and dispensed at fluid flow rates of 0, 8, and 16 mL/min. OMB perfusate at 70% and 90% indicate the volume fraction of oxygen in the OMB emulsion. At 50%, the OMB emulsion's rheological properties are similar to saline. In certain other example embodiments, an OMB concentration between 60%-95% may be used. In certain other example embodiments, an OMB concentration of about 10%-90% may be used. At 90% volume fraction, the OMBs ability to circulate in the IP space degrades due to increased viscosity, but oxygen content is enhanced. It was calculated that perfusing OMBs at 8 mL/min provides sufficient oxygen capacity for a 400 g rat. Perfusing OMBs at 8 mL $min^{-1}$ provides sufficient oxygen capacity considering a 400 g rat. Perfusion at a higher rate (16 mL $min^{-1}$) and introducing a stagnant OMB bolus (0 mL $min^{-1}$). The motility enhancing drug ghrelin is administered (200 mg $kg^{-1}$ dose) in half of the tests via the tail vein catheter 30 minutes prior to anesthetization.

IP Ventilation of Rabbit Model In Vivo:

Male New Zealand White rabbits (n=13, m=2.260±0.196 kg) were weighed and anesthetized by 5% isoflurane gas by nose cone to effect. Rabbits were then intubated with an endotracheal tube and laid in the supine position on a warming pad set at 38° C. to maintain body temperature. The abdomen of the rabbit was shaved, divided into quadrants with a marker, and sterilized. A veterinary monitor was used to monitor and record vitals via two sensors placed rectally; a pulse oximetry sensor was used to measure pulse rate and arterial oxygen hemoglobin saturation ($SpO_2$), and a temperature probe was used for measuring body temperature. The rabbit was given an intramuscular injection of ketamine-xylazine (35-5 mg/kg) and then gradually weaned off isoflurane and allowed to breathe room air. A small incision was made into the abdomen to allow access for placement of infusion and drainage tubing (3.2 mm inner, 4.8 mm outer diameter, Tygon) in the intraperitoneal cavity and then sutured closed. A 12 G indwelling catheter and a 14 G needle connected to pressure transducers were inserted into the IP cavity for measuring intra-abdominal pressure via a data acquisition and custom control system. The control system was designed to use IA pressure and a solenoid fixed to the drainage line to regulate the volume of perfusate administered into the cavity.

Perfusate was pumped through a fluid warmer set at 40.4° C. and into the IP space with a peristaltic pump at 80 mL/min for 3 minutes and then at dose of 12.6 mL/min*kg thereafter. At this time, the endotracheal tube was hermetically sealed to prevent oxygen intake and simulate complete lung failure. The fluids used as a perfusate were oxygenated saline for the control group and OMBs for the experimental group. The survival data for rabbits using saline survived 6.9±0.6 minutes. The OMB treated rabbits survived on average for 18 minutes and one outlier lived for 72 minutes after the trachea tube had been sealed; The outlier 72 minute survival time rabbit had successful circulation and IA pressure below 8 mmHg.

GI Ventilation of Rat Model In Vivo:

The test setup for perfusing the GI is identical to that for perfusing the IP except that the small intestine is resected at the duodenum and distal ileum (with the mesentery left intact). The supply tube is inserted into the resected duodenum, the scavenge tube is inserted into the resected distal ileum, and perfusate is pumped into and through the entire length of the small bowel. Saline with neutral oxygen tension with respect to atmosphere is used as a third perfusate to provide a control for all experiments. Six rats are tested at the given OMB perfusion rate of 8 and 16 mL/min flow rates and the internal pressure over time was measured to find suitable conditions for infusion and scavenging. Results show that internal pressure never surpasses the upper limit of 8 mmHg and the system perfuses saline at the desired rates while maintaining physiological pressure levels in the phantom abdomen.

Figure 7:
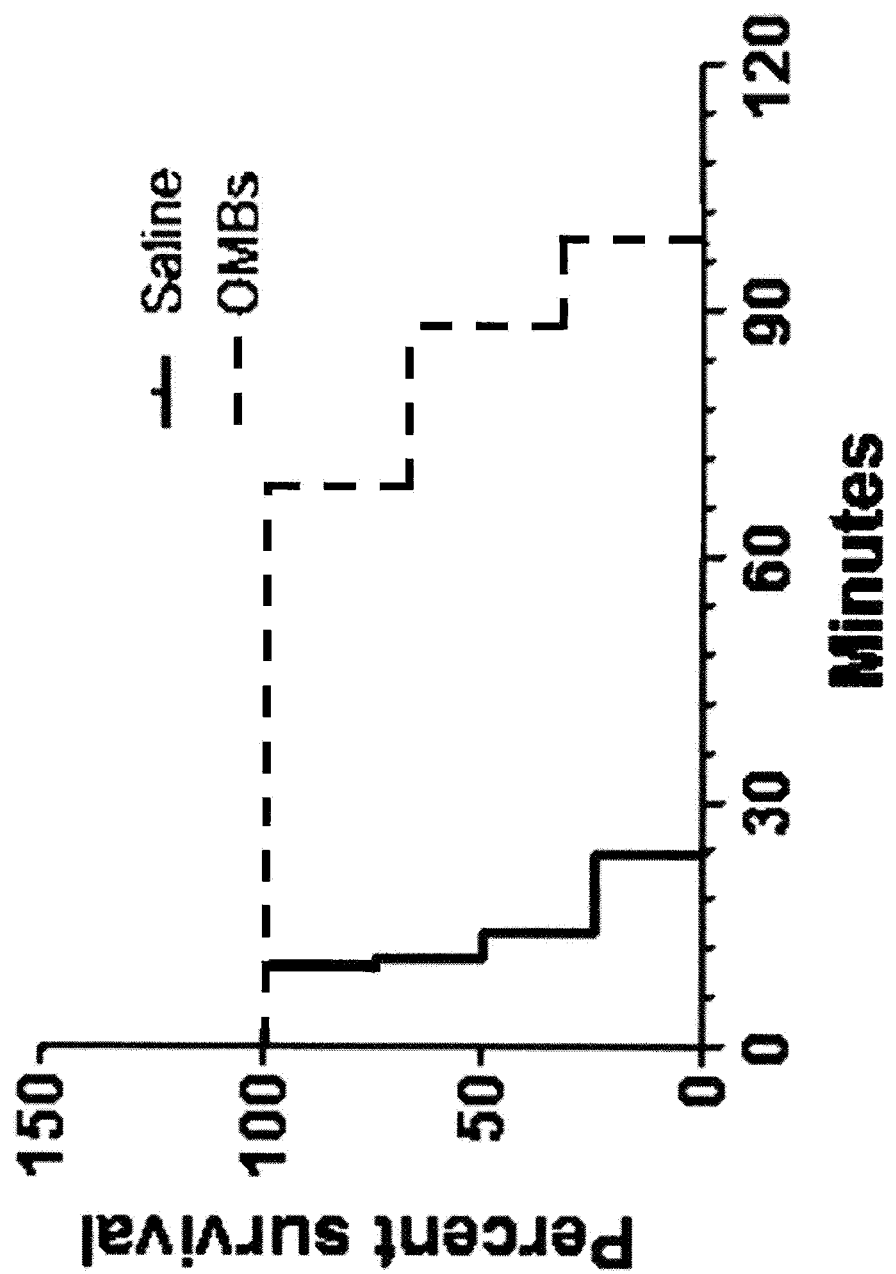
FIG. 7 illustrates a graph of survival rates over time for test subjects with a pneumothorax model and intraperitoneal injection of oxygen microbubbles compared to saline injection according to the invention.

Perfusing OMBs at 8 mL min$^{-1}$ in 400 g rats with a right pneumothorax survival rates are promising over time. FIG. 7 illustrates a graph of survival rates over time for test subjects with a pneumothorax model and intraperitoneal injection of oxygen microbubbles compared to saline injection according to the invention. The fluids used as perfusate were (1) saline as a control or (2) a solution with an OMB concentration of ~50 vol %. Intra-abdominal pressure was measured at the supply tube inlet to avoid high internal pressures that could damage internal organs or the IP catheter seal. Cardiac arrest eventually follows a right pneumothorax and is caused by lack of blood oxygen (hypoxemia) and elevated carbon dioxide levels and subsequent low blood pH (acidosis), which result from pulmonary failure. As shown in FIG. 7, saline control specimens survived for an average of ~14.1 minutes after right pneumothorax in the presence of saline. In comparison, the specimen injected with OMBs survived for an average of ~83.3 minutes after right pneumothorax, which represents a ~8-fold improvement in survivability in comparison to the controls (p<0.5; Gehan-Breslow-Wilcoxon Test). The effectiveness of IP ventilation was established by measuring saturated arterial oxygen fraction (SAO2). Results demonstrate that cardiac arrest in hypoxemic rodents is significantly delayed by intraperitoneal administration of OMBs.

Pleural Cavity Ventilation of Rabbit Model In Vivo:

Male New Zealand White rabbits were weighed and anesthetized by 5% isoflurane gas by nose cone to effect. Rabbits were then intubated with an endotracheal tube and laid in the supine position on a warming pad set at 38° C. to maintain body temperature. The abdomen of the rabbit was shaved, divided into quadrants with a marker, and sterilized. A veterinary monitor was used to monitor and record vitals via two sensors placed rectally; a pulse oximetry sensor was used to measure pulse rate and arterial oxygen hemoglobin saturation ($SpO_2$), and a temperature probe was used for measuring body temperature. The rabbit was given an intramuscular injection of ketamine-xylazine (35-5 mg/kg) and then gradually weaned off isoflurane and allowed to breathe room air. A small incision was made into the abdomen to allow access for placement of infusion and drainage tubing (3.2 mm inner, 4.8 mm outer diameter, Tygon) in the pleural cavity and then sutured closed. A 12 G indwelling catheter and a 14 G needle connected to pressure transducers were inserted into the pleural cavity for measuring pressure via a data acquisition and custom control system as shown in FIG. 6. The control system was designed to use IA pressure and a solenoid fixed to the drainage line to regulate the volume of perfusate administered into the cavity.

Figure 8:
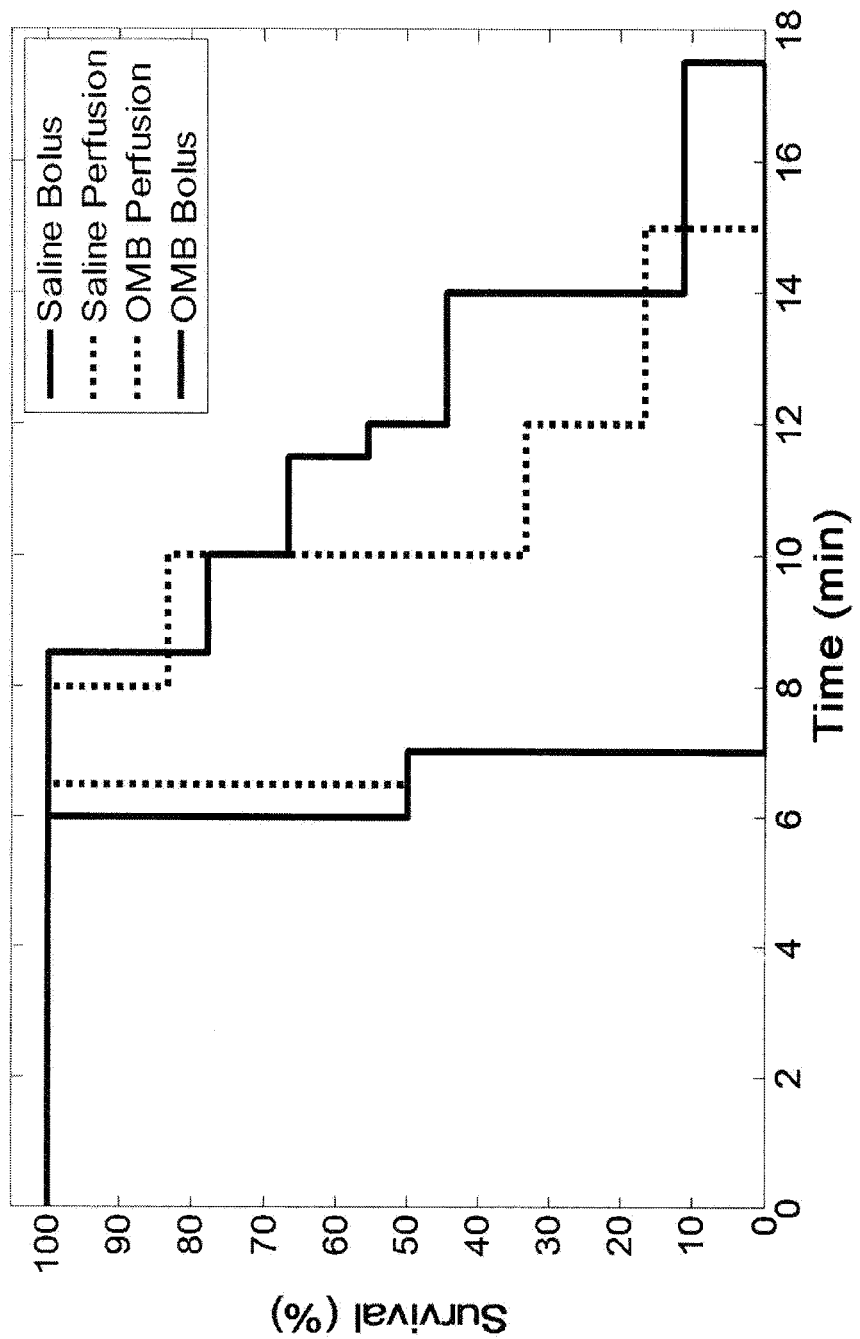
FIG. 8 illustrates a graph of survival rates over time for test subjects with an asphyxiation model and pleural injection of oxygen microbubbles compared to saline injection according to the invention.

Perfusate was pumped through a fluid warmer set at 40.4° C. and into the pleural space. At this time, the endotracheal tube was hermetically sealed to prevent oxygen intake and simulate complete lung failure. The fluids used as a perfusate were oxygenated saline for the control group and OMBs for the experimental group. The survival data for rabbits using saline under a saline bolus or saline perfusion injection survived an average of seven minutes. The OMB perfusion treated rabbits survived on average for 15 minutes and OMB bolus treated rabbits survived on average for 17.5 minutes as shown in FIG. 8.

While the disclosure is susceptible to various modifications and alternative forms, specific exemplary embodiments of the invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A method for administering oxygen to a subject, comprising the steps of:
    inserting at least a portion of a supply tube into an existing gastrointestinal body cavity of the subject, the supply tube having a supply opening and a supply lumen in fluid communication with a reservoir of a supply device, the reservoir positioned outside of the existing gastrointestinal body cavity;
    inserting at least a portion of an outlet tube into the existing gastrointestinal body cavity of the subject, the outlet tube including at least one removal opening, wherein the at least one removal opening is spaced apart from the supply opening by a portion of the existing gastrointestinal body cavity;
    delivering from the supply device a first plurality of microbubbles containing a first gas into the existing gastrointestinal body cavity of the subject, the first gas being at least 50% oxygen by volume; and
    removing a second plurality of microbubbles containing a second gas from the gastrointestinal body cavity of the subject, the second gas being less than 50% oxygen by volume and having a carbon dioxide concentration that is greater than a carbon dioxide concentration of the first gas.

2. The method of claim 1, wherein at least a portion of the first plurality of microbubbles comprises microbubbles 10 micrometers or smaller.

3. The method of claim 1, wherein the portion of the supply tube is inserted into the existing gastrointestinal body cavity of the subject via a surgically created opening.

4. The method of claim 1, wherein the portion of the outlet tube is inserted into the existing gastrointestinal body cavity of the subject via a surgically created opening.

5. The method of claim 1, wherein at least a portion of the first plurality of microbubbles comprises microbubbles from 10 to 25 micrometers in diameter.

6. The method of claim 1, wherein at least a portion of the first plurality of microbubbles comprises microbubbles from 25 to 100 micrometers in diameter.

7. The method of claim 1, wherein at least a portion of the first plurality of microbubbles comprises microbubbles from 100 to 500 micrometers in diameter.

8. A method for administering oxygen to and removing carbon dioxide from a subject, comprising the steps of:
   inserting at least a portion of a supply tube into an existing gastrointestinal body cavity of the subject, the supply tube having a supply opening and a supply lumen in fluid communication with a reservoir of a supply device, the reservoir positioned outside of the existing gastrointestinal body cavity;
   delivering from the supply tube a first plurality of microbubbles containing a first gas into the existing gastrointestinal body cavity of the subject, the first gas having a first oxygen percentage by volume and a first carbon dioxide percentage by volume; and
   removing a portion of the first plurality of microbubbles from the existing gastrointestinal body cavity of the subject, the portion of the first plurality of microbubbles having a second gas, the second gas having a second oxygen percentage by volume and a second carbon dioxide percentage by volume, wherein the first oxygen percentage of the first gas is greater than the second oxygen percentage of the second gas and the second carbon dioxide percentage of the second gas is greater than the first carbon dioxide percentage of the first gas.

9. The method of claim 8, wherein the first plurality of microbubbles comprise microbubbles 10 micrometers or smaller in diameter.

10. The method of claim 8, wherein the portion of the supply tube is inserted into the existing gastrointestinal body cavity of the subject via a surgically created opening.

11. The method of claim 8, wherein the first plurality of microbubbles comprises microbubbles from 10 to 25 micrometers in diameter.

12. The method of claim 8, wherein the first plurality of microbubbles comprises microbubbles from 25 to 100 micrometers in diameter.

13. The method of claim 8, wherein the first plurality of microbubbles comprises microbubbles from 100 to 500 micrometers in diameter.

14. The method of claim 8, wherein the removing the portion of the first plurality of microbubbles from the existing gastrointestinal body cavity of the subject comprises placing at least a portion of an outlet tube into the existing gastrointestinal body cavity of the subject and removing the portion of the first plurality of microbubbles from the existing gastrointestinal body cavity of the subject through the portion of the outlet tube.

15. The method of claim 14, wherein the portion of the outlet tube is inserted into the existing gastrointestinal body cavity of the subject via a surgically created opening.

16. A method for removing carbon dioxide from the tissues of a subject, comprising the steps of: inserting at least a portion of a supply tube into an existing gastrointestinal body cavity of the subject, the supply tube having a supply opening and a supply lumen in fluid communication with a reservoir of a supply device, the reservoir positioned outside of the existing gastrointestinal body cavity; delivering from the supply opening a first plurality of microbubbles containing a first gas into the existing gastrointestinal body cavity of the subject, the first gas having a first carbon dioxide concentration by volume at the time of delivery; and removing a portion of the first plurality of microbubbles from the existing gastrointestinal body cavity of the subject at a second time period after the time of delivery, the portion of the first plurality of microbubbles containing a second gas, the second gas having a second carbon dioxide concentration by volume at the second time period which is greater than the first carbon dioxide concentration by volume at the time of delivery.

17. The method of claim 16, wherein the portion of the supply tube is inserted into the existing gastrointestinal body cavity of the subject via a surgically created opening.

18. The method of claim 16, wherein at least a portion of the first plurality of microbubbles comprises microbubbles 10 micrometers or smaller.

19. The method of claim 16, wherein the portion of the first plurality of microbubbles removed from the existing gastrointestinal body cavity of the subject are removed via an outlet tube.

20. The method of claim 19, wherein the outlet tube is inserted into the existing gastrointestinal body cavity of the subject via a surgically created opening.

* * * * *